United States Patent [19]
Rossignol et al.

[11] Patent Number: 5,935,591
[45] Date of Patent: Aug. 10, 1999

[54] METHOD FOR TREATMENT OF EQUINE PROTOZOAL MYELOENCEPHALITIS WITH THIAZOLIDES

[75] Inventors: Jean-François Rossignol, Clearwater; Marc S. Ayers, Tampa, both of Fla.

[73] Assignee: Romark Laboratories, L.C., Tampa, Fla.

[21] Appl. No.: 09/007,653

[22] Filed: Jan. 15, 1998

[51] Int. Cl.[6] ................................. A01N 25/12
[52] U.S. Cl. ................ 424/405; 424/406; 424/408; 424/470; 424/489; 574/370
[58] Field of Search .................. 424/405, 406, 424/408, 409, 410, 420, 421, 442, 439, 464, 470, 469; 574/370

[56] References Cited

U.S. PATENT DOCUMENTS

| 3,950,351 | 4/1976 | Rossignol et al. | 260/306.8 |
| 5,387,598 | 2/1995 | Rossignol | 574/371 |
| 5,578,621 | 11/1996 | Rossignol | 574/371 |

*Primary Examiner*—Neil S. Levy
*Attorney, Agent, or Firm*—Pendorf & Cutliff

[57] ABSTRACT

A method for treatment or prevention of equine protozoal myeloencephalitis, a condition for which there is presently no effective treatment. The method comprises administering to the infected horse an amount of one or more 2-benzamido-5-nitro-thiazole compounds sufficient to eradicate *Sarcocystis spp.*

29 Claims, No Drawings

METHOD FOR TREATMENT OF EQUINE PROTOZOAL MYELOENCEPHALITIS WITH THIAZOLIDES

BACKGROUND OF THE INVENTION

1. Field of the Invention

The present invention provides a method for treatment or prevention of equine protozoal myeloencephalitis, a condition caused by *Sarcocystis spp.* for which there is presently no effective treatment.

2. Description of the Related Art

Equine protozoal myeloencephalitis (EPM) was initially observed by J. R. Rooney in 1964. Since then, cases have been reported among native horses in most of the United States as well as in Canada, Mexico, Argentina, Panama, and Brazil. During the 1970's, a protozoan was recognized in histopathologic sections of neural tissues of affected horses resulting in the disease being named "equine protozoal myeloencephalitis," but the actual protozoan was not known. In 1991 Dubey showed that EPM was caused by a *Sarcocystis* organism. Subsequently the organism was named *Sarcocystis neurona* because it often develops within neurons.

In 1995, results of polymerase chain reaction (PCR) analysis and work done at the University of Kentucky and at the University of Florida provided strong evidence that the opossum (*Didelphis virginiana*) is the definitive host of *Sarcocystis neurona*. This study revealed a 99.67% homology with the opossum sporocyst, *Sarcocystis falcatula*. It is possible that *S. neurona* will be re-named to *S. falcatula*.

Opossums eat almost anything: dead birds, insects, etc. The feces of the opossum represent a rich source of nutrition for wild birds. Wild birds ingest sporocysts by eating opossum feces. The parasite undergoes asexual reproduction in the blood vessels of the liver, lungs and muscles and then encysts in the bird's muscle tissue, without traveling to the central nervous system. When bird tissue is eaten by the opossum, the parasite undergoes sexual reproduction in the intestinal cells, and forms the infective sporocysts, which are passed in the feces. The opossum does not become sick, but may shed the parasites for months.

The opossum is indigenous to North, Central and South America which coincides with the fact that cases of EPM have only been reported in horses that have lived in areas that the opossum inhabits. Infected horses cannot communicate the disease to other horses; infection occurs when the droppings of opossum or wild birds carrying the disease mix with the feed of the horse, and the horse consumes the feed.

*S. neurona* (*falcatula*) may aberrantly infect a large number of intermediate hosts such as it does in the horse, with reports of infection in dogs, sheep, cats, mink, raccoons, striped skunks, golden hawks, rhesus monkeys and chickens. In addition to the predator-prey life cycle, there is some speculation there are transport vectors which may play a role in this disease, including cockroach, and wild birds such as pigeon, finch, canary, grosbeak, and budgerigar which form sarcocysts after ingestion of the sporocysts of *S. falcatula*.

Horses represent an aberrant host of this protozoan. Sporocysts are ingested, but never encyst in the tissues of the horse. Instead, they migrate to the central nervous system, where they continue to undergo asexual reproduction intracellularly in neurons, without forming tissue cysts. Central nervous system (CNS) lesions in the horse are often extensive, and may be microscopic to several centimeters wide. The brainstem and spinal cord are affected most often.

The actual signs of abnormality depend on the location and the extent of colonies. The disease may be "encephalitis" when effects of damage are seen in the brain; it may be "myelitis" when effects of damage are seen in the spine; or may be "encephalomyelitis" or "myeloencephalitis" when both the brain and the spine are affected. Symptoms of EPM may be attributed to either the body's inflammatory reaction (swelling) to the parasites or to actual destruction of nerve structures within the CNS. Sometimes, there is a discrete loss of specific muscle groups (neurogenic atrophy). EPM might also cause abortion in pregnant mares.

Exposure of horses to EPM occurs at an average rate of about 50%, but approaches 80–90% among the racing equine population. Only a relatively small number of infected horses actually develop disease due to parasite damage in the central nervous system.

Most EPM-affected horses are treated with antiprotozoal drugs for at least 4 months, and improve 1–2 grades in neurologic symptoms. The dosage recommendations for the treatment of EPM are pyrimethamine antimalarial medications (1.0 mg/kg daily), in combination with a sulfonamide antibiotic, for a minimum duration of 120 days. This combination causes a sequential blockade of folate metabolism in apicomplexan protozoa. This treatment protocol can be expensive, costing $400/month to $850/month.

This antimalarial/antibiotic treatment does not appear to eliminate the *Sarcocystis neurona* organism; it merely constrains the organism until the body is able to eliminate it. Some horses are not able to eliminate the organism—they get better because the parasite is inhibited, but they are at risk for further problems if their immune system is compromised again in the future. Recovered horses must be retreated strategically on a frequent basis for the remainder of their lives. Only a small percentage of horses make a complete recovery, some horses do not respond to treatment whatsoever, and a significant number of horses eventually relapse and develop further active EPM.

Recent discussions concerning EPM have led to reports of using tetracyclines in some cases that continue to be cerebral spinal fluid positive (CSF+) even after many months (6 months or longer) with the sulfa/pyrimethamine combination. This use is based upon tetracycline's inhibitory effect on protein synthesis, however, no controlled trials have been performed at this time. The only reported antiprotozoal use of tetracycline was documented in sheep which received 30 mg/kg to treat a different *Sarcocystis spp.* infection. This an extremely high dosage, and is not recommended for use in horses. It is not clear why using tetracycline, a bacteriostatic agent, would be curative.

In addition to the low success rate, a further problem with the presently available therapy concerns undesirable side effects of the therapy such as anemia, leukopenia, and colitis. Some horses actually get worse during treatment, presumably because the administration of a large dose of medication triggers development of an inflammatory response due to the killing of large numbers of parasite at one time. The spinal canal is a very narrow space with limited room for expansion due to inflammation.

At this time, there is no vaccine available to protect against the disease, though this is currently an area of research.

Accordingly, it is an object of the present invention to provide therapeutic compounds useful in the treatment of animals afflicted with, or at risk of being afflicted with, equine protozoal myeloencephalitis.

It is a further object of the invention to provide therapeutic compounds for treatment of protozoal and helminth infections in horses which therapeutic compounds are well tolerated by horses when administered in therapeutically effective amounts.

SUMMARY OF THE INVENTION

The present invention is based on the discovery of an effective method for treatment or prevention of equine protozoal myeloencephalitis in a horse, the method comprising administration of a pharmaceutical composition containing as active agent one or more of 2-benzamido-5-nitro-thiazole compounds of formula (I):

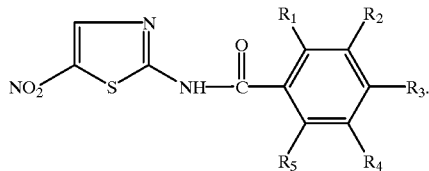

in which at least one of the symbols $R_1$, $R_2$, $R_3$, R4 and $R_5$ represents an acyloxy group, preferably an acetoxy or propionoxy group, or a hydroxy group whereas the remaining symbols represent hydrogen or one of said remaining symbols represents an alkoxy group.

The pharmaceutical composition may be in a form suitable for oral administration, as a solid dosage form, a liquid suspension, or a paste.

The foregoing has outlined rather broadly the more pertinent and important features of the present invention in order that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other pharmaceutical compositions and methods for treatment for carrying out the same purposes of the present invention. It should also be realized by those skilled in the art that such equivalent formulations and methods do not depart from the spirit and scope of the invention as set forth in the appended claims.

DETAILED DESCRIPTION OF THE INVENTION

The method for treatment or prevention of equine protozoal myeloencephalitis according to the present invention comprises administration of a pharmaceutical composition comprising, as active agent, one or more derivatives of 2-benzamido-5-nitro-thiazole represented by the following formula I.

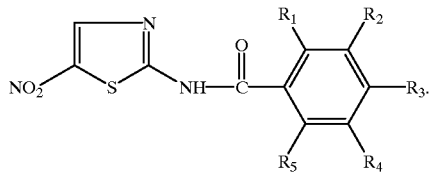

in which at least one of the symbols $R_1$, $R_2$, $R_3$, R4 and $R_5$ represents an acyloxy group or a hydroxy group, whereas the remaining symbols represent hydrogen or one of said remaining symbols represents an alkoxy group can be administered to animals afflicted with equine protozoal myeloencephalitis for effective eradication of protozoa.

Representative examples of compounds of formula (I) include:
2-(2'-acetoxy)-benzamido-5-nitro-thiazole;
2-(2'-propionoxy)-benzamido-5-nitro-thiazole;
2-(2'-hydroxy)-benzamido-5-nitro-thiazole;
2-(3'-acetoxy)-benzamido-5-nitro-thiazole;
2-(3'-propionoxy)-benzamido-5-nitro-thiazole;
2-(3'-hydroxy)-benzamido-5-nitro-thiazole;
2-(4'-acetoxy)-benzamido-5-nitro-thiazole;
2-(4'-propionoxy)-benzamido-5-nitro-thiazole;
2-(4'-hydroxy)-benzamido-5-nitro-thiazole;
2-(2'-acetoxy, 4'-hydroxy)-benzamido-5-nitro-thiazole;
2-(2'-propionoxy, 4'-hydroxy)-benzamido-5-nitro-thiazole; and
2-(2', 4'-dihydroxy)-benzamido-5-nitro-thiazole.

Preferred examples of compounds of formula (I) include desacetyl-nitazoxanide of formula (II):

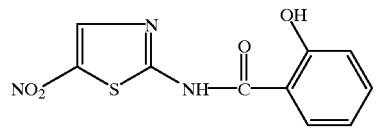

and nitazoxanide of formula (III)

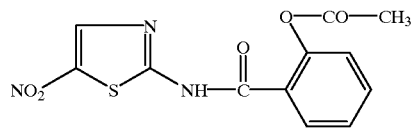

Nitazoxanide, the compound of formula III, sometimes referred to hereafter as NTZ or compound PH 5776, is the generic name for 2-(acetolyloxy)-N-(5-nitro 2-thiazoly) benzamide, a compound first synthesized by Rossignol and Cavier in 1975 and subsequently shown to have activity against a number of protozoan and helminthic pathogens. Nitazoxanide has a molecular weight of 307.2; it appears as odorless yellow granules with a melting point of 202–204° C.; it is very poorly soluble in water, either and methyl benzene; poorly soluble in ethanol, chloroform and acetic acid; fairly soluble in dioxane and acetone and easily soluble in pyridine. Solubilisation in DMSO is recommended.

In 1980, Euzeby et al reported the cestocidal effect of a single oral dose of nitazoxanide against *Moniezia expansa, Avitellina centripunctata, Stilesia globipunctata* and *Thysanezia ovilla* in sheep, *Dipylidium caninum* and *Taenia pisiformis* in dogs and *Taenia taeniaeformis* in cats. In addition, when using repeated doses of the drug, efficacy against gastrointestinal nematodes of dogs such as *Uncinaria stenocephala* and *Trichuris vulpis* was also observed. In 1982 Cavier and Rossignol reported the single dose activity of nitazoxanide against *Hymenolepis nana* in mice and the effect of repeated doses of the drug against *Syphacia obvelata* in mice. More recently Dubreuil et al. reported that nitazoxanide was also effective against Gram positive bacteria such as *Staphylococcus aureus* and facultative and obligate anaerobic Gram positive and Gram negative bacteria.

The preparation and certain uses of this compound are disclosed in U.S. Pat. No. 3,950,351, as well as in publications made by the present inventor.

Desacetyl-nitazoxanide, the compound of formula II, is sometimes referred to as tizoxanide or d-NTZ, and is a metabolite of nitazoxanide. In WO 95/28393, the present inventor disclosed a method for the manufacture of pure compound of formula II, as well as the use of the composition containing a mixture of compounds of formula II and III.

The compound(s) of formula I may be administered in either a solid dosage form or an aqueous suspension, and it is preferred that the pharmaceutical composition contain the effective dose of the active agent in the form of solid particles having a particle size smaller than 200 $\mu$m and containing one or more compounds of formula I, such as mixtures of compounds II and III, the mean particle size of the said active solid particles being greater than 10 $\mu$m as determined by a Coulter Counter LS 100. This equipment uses laser light at 750 nm to size particles from 0.4 to 900 $\mu$m in diameter by light diffraction. The samples are measured in water with a small amount of Triton X-100 in order to increase the wettability and deflocculate the powder.

Advantageously, the mean particle size of the active solid particles is between 10 and 100 $\mu$m, preferably between 20 and 50 $\mu$m. In accordance with a preferred embodiment of the composition, less than 10% of the active solid particles has a particle size smaller than 5 $\mu$m.

The invention also relates to pharmaceutical compositions described above which contain advantageously at least one pharmaceutically acceptable acid. Examples of such acids are: citric acid, glutamic acid, succinic acid, ethanesulfonic acid, acetic acid, tartric acid, ascorbic acid, methanesulfonic acid, fumaric acid, adipic acid, malic acid and mixtures thereof. Citric acid is very appropriate. The presence of said acid improves the stability of the active agent or agents.

The ratio of the weight of pharmaceutically acceptable acid/the weight of said active solid particles is advantageously between 0.01 and 0.5, preferably between 0.03 and 0.2. Advantageously, the amount of acid is sufficient for adjusting the pH of the suspension between 2 and 6, preferably between 3 and 5, most preferably between 3.5 and 4.5.

The active agent or agents used in the solid dosage form or suspension is advantageously a mixture of solid particles of compounds of formula 11 and of formula III with a particle size smaller than 200 $\mu$m, the weight content of compound of formula III with respect to the weight of compounds of Formula II and of Formula III of said mixture being between 0.5 and 20%, preferably between 0.5 and 10%.

Techniques for preparation of, and preferred examples of, solid and liquid dosage forms of the pharmaceutical composition are disclosed in U.S. Pat. Nos. 3,950,351; 3,957,812; 4,315,018; 5,387,598; and WO/95/28393, the disclosures of which are incorporated herein by reference. The compositions contain advantageously a wetting agent and possibly a starch derivative such as those disclosed in U.S. Pat. No. 5,578,621, the content of which is incorporated herein by reference for disclosing possible wetting agents and starch derivatives. The wetting agent as described in U.S. Pat. No. 5,578,621 serves as a dispersing agent.

Such pharmaceutical compositions, either as solid or liquid dosage forms or as pastes or ointments, can optionally contain additional active agents such as antibiotics, antiviral agents, vitamins, or proton pump inhibitors. While it is not advantageous, it is also possible that such pharmaceutical formulations may contain active solid particles of compound of Formula II and/or compound of Formula III which are larger than 200 $\mu$m.

The compositions can contain excipients known as such for the purpose of preparing forms suitable for oral administration. The efficacy and the safety of the pharmaceutical compositions disclosed hereabove were excellent in animals and/or in humans.

Treatment of animals afflicted with, or at risk of being afflicted with, EPM will now be discussed in greater detail. Diagnostic confirmation of EPM requires finding antibodies or parasitic DNA in either the blood or spinal fluid. The best test involves the collection of a spinal fluid sample which is tested for antibodies against *Sarcocystis neurona;* this test is the western immunoblot. This test relies on the fact that, during active EPM, antibodies are being produced against *Sarcocystis neurona* within the spine and brain. Antibodies are only found in the spinal fluid in the face of active disease.

A negative blood test reduces the likelihood that EPM is involved. A positive blood test only indicates that the horse has been exposed to the parasite and the majority of exposed horses do not develop clinical disease. Although spinal fluid samples are more difficult to obtain, they more reliably confirm the presence of the parasite in the spinal fluid, thereby, confirming the clinical disease and need for treatment.

An even more reliable test of the spinal fluid for the actual presence of the *Sarcocystis neurona* is a test known as a PCR (which can also be done with blood and tissues). This test is more expensive and is best used when trying to determine whether the treatment has been successful.

Treatment is aimed at killing the protozoa and its offspring (the merozoites) whether they be in the intestinal tract, blood, cerebral spinal fluid or other tissues, and decreasing the inflammation in the nervous tissue. In areas where *Sarcocystis spp.* are known to be prevalent, a horse may be treated presumptively for eradication of the protozoa and prevention of the disease. Preventative treatment would comprise administering to a horse 25 to 200 mg/kg of body weight of a compound or mixture of compounds of formula (I) for one or more days, preferably three to seven days, every two to four months. The length of treatment varies according to the severity of the disease, damage present and response to treatment. The treatment can vary from weeks to months. Supplementation with vitamin E (5,000–9,000 IU, orally every 12 hours), folic acid and thiamine may be a helpful adjunct treatment.

When the horse has an acute onset of EPM which results in dramatic and progressive clinical signs, the use of anti-inflammatory medications such as banamine phenylbutazone or banamine (1.1 mg/kg 1–2 times daily for 3–7 days), may be helpful. Dexamethasone may be used parenterally in severely affected horses at a dose rate of 0.05 mg/kg bid or sometimes empirically at 50 mg. bid. However, corticosteroids should be used judiciously. The exacerbation of signs in stressed patients and reports of horses with EPM showing a worsening of signs following the use of these medications suggest immunosuppression should be avoided. Ancillary treatments may include padded helmets, slings, good supportive care and a deeply bedded stall.

Ideally, CSF should be obtained and determined to test negative by immunoblot or PCR before the treatment is discontinued—see Fenger C K, Granstrom D E, Langemeier J L, Stamper S. Detection of *Sarcocystis neurona* in cerebrospinal fluid of horses by nested polymerase chain reaction. J. Vet. Diagn. Invest., in press.

Nitazoxanide and tizoxanide have been tested in an in vitro test system for activity against *Sarcocystis spp.*, and it was determined that both drugs are highly active in inhibiting the growth of the protozoa with 50% inhibitory concentrations of approximately 0.475 µg/ml. Based upon this finding, horses were treated with a pharmaceutical formulation of nitazoxanide in order to assess the safety, tolerance, pharmacokinetics (including drug concentration in the CSF) and efficacy of the drug in horses.

EXAMPLE

Conditions and treatment regimens for 5 horses treated with nitazoxanide, one with EPM and 4 others with antibodies for *Sarcocystis spp.* in their blood, are set forth below. All dosages were administered in solid (tablet) form.

Horse #1–2 yr. thoroughbred stallion

This horse was positive for *Sarcocystis* infection in CSF and serum. It exhibited symptoms of ataxia, and weakness in its rear limbs with a neurological deficiency present. The horse was dosed from day 1 to day 6 with 50 mg/kg Nitazoxanide, then day 9 to day 16 with 100 mg/kg Nitazoxanide, then day 18 to day 25 with 150 mg/kg test drug. The horse injured both hocks on day 12 by kicking the stall, resulting in edema of both rear limbs. On days 15 and 16 he was slow to finish eating feed. On day 17 he was back to eating normally. Symptoms of EPM were gone by day 10 and have not returned. Monitoring was continued for 23 days, with no reoccurrence of symptoms.

Horse #2–3 yr. thoroughbred mare

This horse was positive for *Sarcocystis* infection in serological testing for antibody, showing no symptoms of the disease. The horse was dosed on days 1 to 6 with 75 mg/kg nitazoxanide, on days 9 to 16 with 100 mg/kg Nitazoxanide, and on days 18 to 25 with 150 mg/kg nitazoxanide. The horse tolerated the drug well at all dose levels.

Horse #3–13 yr. thoroughbred mare

At the onset of the experiment this horse was positive for *Sarcocystis* infection in serological testing for antibody, but showed no symptoms of the disease. The horse was dosed on days 1 to 6 with 75 mg/kg nitazoxanide, on days 9 to 16 with 100 mg/kg nitazoxanide, and on days 18 to 27 with 150 mg/kg nitazoxanide. The horse tolerated the drug well at all dose levels.

Horse #4–2 yr. thoroughbred mare

This horse was positive for *Sarcocystis* in serological testing for antibody, showing no symptoms of the disease. The horse was dosed on days 1 to 6 with 75 mg/kg Nitazoxanide, on days 9 to 16 with 100 mg/kg nitazoxanide, and on days 18 to 27 with 150 mg/kg nitazoxanide. The horse tolerated the drug well at all dose levels.

Horse #5–6 mo. thoroughbred mare

This horse was positive for *Sarcocystis* in serological testing for antibody, showing no symptoms of the disease. The horse was dosed on days 1 to 6 with 75 mg/kg nitazoxanide, on days 9 to 16 with 100 mg/kg Nitazoxanide, and on days 18 to 27 with 150 mg/kg nitazoxanide. The horse tolerated the drug well at all dose levels.

Due to the history of the stable in which these horses were quartered having a high incidence of EPM (three horses having died of EPM within the past year), and due to the indication of probable active disease process in Horse #1, it was surprising that there was an absence of any symptoms in the five horses at the end of the trial and during the 30-day period after the trial. One would have expected at least Horse #1 to have progressed to death or to have exhibited symptoms so devastating that euthanasia would be necessary for humane reasons.

Furthermore, it is important to note that no signs of toxicity were seen in any of these horses, leading to the conclusion that nitazoxanide is suitable for the treatment of horses from the perspective of its safety and tolerance.

Finally, HPLC assays of the blood and cerebral spinal fluid of horses following oral administration of pharmaceutical formulations of nitazoxanide have revealed that an active metabolite of nitazoxanide is present in both the blood and the cerebral spinal fluid.

Based on tests with other animals, it has been shown that compounds of Formula I in which at least one of the symbols $R_1$, $R_2$, $R_3$, $R_4$ and $R_5$ represents an acyloxy group or a hydroxy group, whereas the remaining symbols represent hydrogen or one of said remaining symbols represents an alkoxy group, can be administered to animals afflicted with protozoal and helminth infections for the purpose of eliminating the parasites. The question of tolerance of this family of medications in a horse and effectiveness in a horse has been proven by experimentation, only a portion of which is set forth herein.

With respect to the above description then, it is to be realized that the optimum formulations and methods of the invention are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Now that the invention has been described,

What is claimed is:

1. A process for treating a horse afflicted with, or at risk of being afflicted with, equine protozoal myeloencephalitis which comprises administering to the infected animal an amount of one or more 2-benzamido-5-nitro-thiazole compounds of the formula (I):

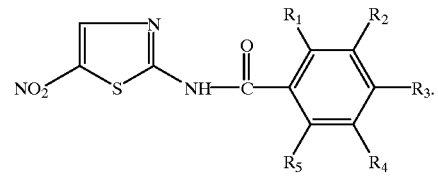

wherein at least one of the symbols $R_1$, $R_2$, $R_3$, $R_4$ and $R_5$ represents an acyloxy group or an hydroxy group and the remaining symbols represent hydrogen or one of the remaining symbols represents an alkoxy group or an hydroxy group, such amount being sufficient to eradicate *Sarcocystis spp.*

2. A process as in claim 1, wherein said acyloxy group is selected from the group consisting of an acetoxy group and a propionyloxy group.

3. A process as in claim 1, wherein only one of the symbols $R_1$, $R_2$, $R_3$, R4 and $R_5$ represents an acyloxy group.

4. A process as in claim 1, wherein two of the symbols $R_1$, $R_2$, $R_3$, R4 and $R_5$ represent an acyloxy group.

5. A process as in claim 1, wherein only one of the symbols $R_1$, $R_2$, $R_3$, R4 and $R_5$ represents an hydroxy group.

6. A process as in claim 1, wherein two of the symbols $R_1$, $R_2$, $R_3$, $R_4$ and $R_5$ represents an hydroxy group.

7. A process as in claim 1, wherein the dosage of said 2-benzamido-5-nitro-thiazole compounds averages from 25 to 200 mg/kg of body weight during the period of treatment.

8. A process as in claim 1, wherein said process is carried out over a period of from 5 days to 3 months.

9. A process as in claim 1, wherein said process is carried out over a period of from 7 days to 30 days.

10. The process of claim 1, wherein the 2-benzamido-5-nitro-thiazole compound is 2-(2'-acetoxy)-benzamido-5-nitro-thiazole.

11. The process of claim 1, wherein the 2-benzamido-5-nitro-thiazole compound is 2-(2'-propionyloxy)-benzamido-5-nitro-thiazole.

12. The process of claim 1, wherein the 2-benzamido-5-nitro-thiazole compound is 2-(2'-hydroxy)-benzamido-5-nitro-thiazole.

13. A method as in claim 1, wherein said 2-benzamido-5-nitro-thiazole compound is in the form of particles with a mean particle size of between 10 and 200 μm.

14. A method as in claim 13, wherein said 2-benzamido-5-nitro-thiazole compound is in the form of particles with a mean particle size of between 20 and 50 μm.

15. A method as in claim 13, wherein less than 10% of said solid particles have a particle size larger than 100 μm.

16. A method as in claim 13, wherein said 2-benzamido-5-nitro-thiazole compound is administered in the form of a pharmaceutical composition comprising said 2-benzamido-5-nitro-thiazole compound, and wherein said pharmaceutical composition further contains at least one pharmaceutically acceptable acid.

17. A method as in claim 16, wherein said pharmaceutically acceptable acid is selected from the group consisting of citric acid, glutamic acid, succinic acid, ethanesulfonic acid, acetic acid, tartric acid, ascorbic acid, methanesulfonic acid, fumaric acid, adipic acid, malic acid and mixtures thereof.

18. A method as in claim 16, wherein the ratio of the weight of pharmaceutically acceptable acid/the weight of said solid particles is between 0.01 and 0.5.

19. A method as in claim 16, wherein said particles of active agent include a granulating agent selected from the group consisting of polyvinylpyrrolidone, water, alcohol, sucrose hydroxyl cellulose and mixture thereof.

20. A method as in claim 1, wherein said 2-benzamido-5-nitro-thiazole agent is a mixture of 2-(2'-acetolyloxy)-benzamido-5-nitro-thiazole and 2-(2'-hydroxy)-benzamido-5-nitro-thiazole.

21. A process for treating a horse afflicted with a protozoal or helminth infection, said process comprising administering to the infected horse an eradicating effective amount of one or more 2-benzamido-5-nitro-thiazole compounds of the formula (I):

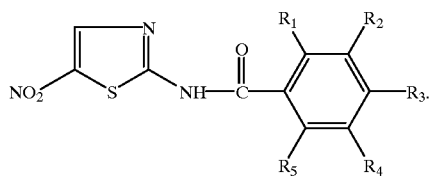

wherein at least one of the symbols $R_1$, $R_2$, $R_3$, $R_4$ and $R_5$ represents an acyloxy group or a hydroxy group and the remaining symbols represent hydrogen or one of the remaining symbols represents an alkoxy group.

22. A process as in claim 21, wherein said acyloxy group is selected from the group consisting of an acetoxy group and a propionyloxy group.

23. A process as in claim 21, wherein the dosage of said 2-benzamido-5-nitro-thiazole compounds averages from 25 to 200 mg/kg body weight during the period of treatment.

24. A process as in claim 21, wherein said process is carried out over a period of from 5 days to 3 months.

25. A process as in claim 21, wherein said process is carried out over a period of from 7 days to 30 days.

26. A process as in claim 21, wherein the 2-benzamido-5-nitro-thiazole compound is 2-(2'-acetoxy)-benzamido-5-nitro-thiazole.

27. A process as in claim 21, wherein the 2-benzamido-5-nitro-thiazole compound is 2-(2'-propionyloxy)-benzamido-5-nitro-thiazole.

28. A process as in claim 21, wherein the 2-benzamido-5-nitro-thiazole compound is 2-(2'-hydroxy)-benzamido-5-nitro-thiazole.

29. A process for treating a horse infected with *Sarcocystis spp.*, which comprises administering to the infected animal an amount of one or more 2-benzamido-5-nitro-thiazole compounds of the formula (I):

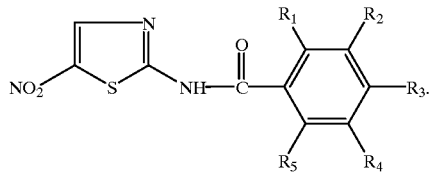

wherein at least one of the symbols $R_1$, $R_2$, $R_3$, R4 and $R_5$ represents an acyloxy group or an hydroxy group and the remaining symbols represent hydrogen or one of the remaining symbols represents an alkoxy group or an hydroxy group, such amount being sufficient to eradicate *Sarcocystis spp.*

* * * * *